US007025911B2

(12) United States Patent
Suzuki et al.

(10) Patent No.: US 7,025,911 B2
(45) Date of Patent: Apr. 11, 2006

(54) MANUFACTURING METHOD FOR ORAL QUICK-DISSOLVING SEAMLESS CAPSULE

(75) Inventors: Katsuhiko Suzuki, Hamamatsu (JP); Masayuki Ikeda, Hamamatsu (JP)

(73) Assignee: Freund Corporation, Tokyo (JP)

( * ) Notice: Subject to any disclaimer, the term of this patent is extended or adjusted under 35 U.S.C. 154(b) by 234 days.

(21) Appl. No.: 10/659,511

(22) Filed: Sep. 10, 2003

(65) Prior Publication Data

US 2004/0051192 A1   Mar. 18, 2004

Related U.S. Application Data

(60) Provisional application No. 60/414,078, filed on Sep. 27, 2002.

(30) Foreign Application Priority Data

Sep. 13, 2002 (JP) ............................. 2002-268714

(51) Int. Cl.
   *B29B 9/10* (2006.01)
(52) U.S. Cl. .......................................... 264/4; 264/4.4
(58) Field of Classification Search .................... 264/4, 264/4.4
   See application file for complete search history.

(56) References Cited

U.S. PATENT DOCUMENTS

| 5,209,978 A | * | 5/1993 | Kosaka et al. ............. 428/402.2 |
| 5,254,294 A | * | 10/1993 | Wunderlich et al. ............ 264/4 |
| 5,288,550 A | | 2/1994 | Sakato |
| 5,650,232 A | | 7/1997 | Glenn et al. |
| 6,719,933 B1 | * | 4/2004 | Nakamura et al. ............. 264/14 |
| 2003/0195246 A1 | * | 10/2003 | Nakamura et al. ........... 514/469 |
| 2005/0079215 A1 | * | 4/2005 | Schleifenbaum et al. ... 424/456 |

FOREIGN PATENT DOCUMENTS

| EP | 0228067 A2 | 7/1987 |
| JP | 59011589 | 1/1984 |
| JP | 62176536 | 8/1987 |
| JP | 62180744 | 8/1987 |
| JP | 4322740 | 11/1992 |
| JP | 4322741 | 11/1992 |
| JP | 4338230 | 11/1992 |
| JP | 5138012 | 6/1993 |
| JP | 200274 A | 8/1993 |

(Continued)

OTHER PUBLICATIONS

International Search Report for PCT/JP03/11649.

*Primary Examiner*—Mary Lynn Theisen
(74) *Attorney, Agent, or Firm*—Hoffmann & Baron, LLP

(57) ABSTRACT

A manufacturing method for oral quick-dissolving capsules, includes the steps of: preparing a core liquid that contains a filler material; preparing a shell liquid by having dissolved therein a shell material that includes one or more plasticizer and a shell forming agent; supplying to a multiple nozzle having an inner nozzle and an outer nozzle, and forming multilayer liquid drops by extruding the multilayer liquid drops from the multiple nozzle; hardening the shell liquid by bringing the multilayer liquid drops into contact with a hardening liquid; separating the seamless capsules from the hardening liquid; and drying their surface to form seamless capsules. The seamless capsules have a particle diameter of 1 to 10 mm, a mass ratio of shell material to filler material of 5:95 to 70:30, and the amount of added plasticizer is 20 to 70% by mass with respect to the total amount of the shell material, excluding water.

8 Claims, 1 Drawing Sheet

FOREIGN PATENT DOCUMENTS

| | | |
|---|---|---|
| JP | 5200274 | 8/1993 |
| JP | 5200275 | 8/1993 |
| JP | 5200276 | 8/1993 |
| JP | 5228360 | 9/1993 |
| JP | 6134292 | 5/1994 |
| JP | 6154587 | 6/1994 |
| JP | 8010313 | 1/1996 |
| JP | 8026976 | 1/1996 |
| JP | 9155183 | 6/1997 |
| WO | WO 02/13819 A1 * | 2/2002 |

* cited by examiner

MANUFACTURING METHOD FOR ORAL QUICK-DISSOLVING SEAMLESS CAPSULE

CROSS-REFERENCE TO RELATED APPLICATIONS

This application is based on Japanese Patent Application No. 2002-268714 filed on Sep. 13, 2002, and U.S. Provisional Application Serial No. 60/414,078 filed on Sep. 27, 2002, the contents of which are incorporated herein by reference.

BACKGROUND OF THE INVENTION

1. Field of the Invention

The present invention relates to a manufacturing method for a seamless capsule in which a filler material (content) such as a food, health food, pharmaceutical, flavoring, or condiment, is encapsulated by a shell material such as gelatin or agar. In particular, the present invention relates to a manufacturing method suitable for manufacturing an oral quick-dissolving seamless capsule whose shell breaks easily in the oral cavity and dissolves quickly in the mouth to release the filler material into the oral cavity.

2. Background Art

Conventionally, as a technology for manufacturing capsules without seams in the shell, that is, a seamless capsule, and in particular, as a technology suitable for manufacturing a capsule being smaller than a typical soft capsule and larger than a microcapsule, methods and apparatuses for producing seamless capsules enclosing a liquid inner layer have been proposed in the following citations. In these citations, multilayer liquid drops are formed by extruding a multilayer jet from a coaxial multiple nozzle such as a double nozzle, triple nozzle, or the like. The outermost liquid layer of the multilayer liquid drop is hardened by bringing it into contact with a hardening liquid to form a shell.

(1) Japanese Unexamined Patent Application, First Publication, No. Sho 59-11859
(2) Japanese Unexamined Patent Application, First Publication, No. Sho 62-176536
(3) Japanese Unexamined Patent Application, First Publication, No. Sho 62-180744
(4) Japanese Unexamined Patent Application, First Publication, No. Hei 4-322740
(5) Japanese Unexamined Patent Application, First Publication, No. Hei 4-322741
(6) Japanese Unexamined Patent Application, First Publication, No. Hei 5-228360
(7) Japanese Unexamined Patent Application, First Publication, No. Hei 4-338230
(8) Japanese Unexamined Patent Application, First Publication, No. Hei 5-200274
(9) Japanese Unexamined Patent Application, First Publication, No. Hei 5-200275
(10) Japanese Unexamined Patent Application, First Publication, No. Hei 5-200276
(11) Japanese Unexamined Patent Application, First Publication, No. Hei 5-138012
(12) Japanese Unexamined Patent Application, First Publication, No. Hei 6-134292
(13) Japanese Unexamined Patent Application, First Publication, No. Hei 6-154587
(14) Japanese Unexamined Patent Application, First Publication, No. Hei 8-10313
(15) Japanese Unexamined Patent Application, First Publication, No. Hei 8-26976
(16) Japanese Unexamined Patent Application, First Publication, No. Hei 9-155183

Recently, in the field of foods such as sweets, functional foods, or luxury foods and the like, oral quick-dissolving capsules that have a shell easily broken in the oral cavity to release into the oral cavity a filler material such as a food, pharmaceutical, flavoring or the like encapsulated by a shell have been under development. In the medical field, because they can be easily taken without water, this type of oral quick-dissolving capsule has become the focus of attention as a means of delivering medicine to the elderly or infants who have a weakened swallowing capacity or difficulty taking pills. Attempts are being made to manufacture oral quick-dissolving capsules using the manufacturing methods for seamless capsules described above.

However, in manufacturing oral quick-dissolving capsules, manufacture becomes difficult when the shell is made thin and easily dissolved in the oral cavity in order to form a shell that breaks easily in the oral cavity. The reasons are that during manufacture the shell may not be sufficiently hardened, the shell strength may be weak even if it is sufficiently hardened, and the capsule may be deformed or easily crushed during separation from the hardening liquid. In contrast, when a sufficient shell strength is imparted to the shell, the obtained product becomes difficult to break in the oral cavity and an adequate oral quick-dissolving property is not obtained.

In such conventional technology, it is difficult to manufacture a product that has, on the one hand, the oral quick-dissolving property of easily breaking down in the oral cavity, while on the other hand, does not cause problems during manufacture such as incomplete hardening of the shell or being crushed.

In consideration of the problems described above, it is an object of the present invention to provide a manufacturing method for oral quick-dissolving seamless capsules in which a product can be manufactured that has the oral quick-dissolving property of easily breaking down in the oral cavity and does not cause problems during manufacture such as incomplete hardening of the shell or being crushed.

BRIEF SUMMARY OF THE INVENTION

A manufacturing method for oral quick-dissolving seamless capsules according to an aspect of the present invention, includes the steps of:

preparing a core liquid containing a filler material;

preparing a shell liquid containing a shell material that includes one or more plasticizer selected from a group consisting of glycerin, propylene glycol, and polyethylene glycol, and a shell forming agent;

supplying to a multiple nozzle, which has an inner nozzle and an outer nozzle that surrounds the inner nozzle, the core liquid so as to be extruded from the inner nozzle, and the shell liquid so as to be extruded from the outer nozzle, in order to form multilayer liquid drops by extruding a multilayer jet from the multiple nozzle;

forming seamless capsules by hardening the shell liquid of the multilayer liquid drops by reacting the shell liquid with a hardening liquid flowing through a pass, and coating the core liquid with the shell material;

separating the seamless capsules from the hardening liquid; and removing the hardening liquid adhering to surfaces of the seamless capsules separated from the hardening liquid and drying the surfaces to form seamless capsules that do not substantially stick to each other;

wherein seamless capsules are manufactured to have a particle diameter of 1 to 10 mm, a mass ratio of shell material to filler material of 5:95 to 70:30, and the amount of added plasticizer is 20 to 70% by mass with respect to the total amount of the shell material, excluding water.

According to this method, it is possible to manufacture oral quick-dissolving seamless capsules that have the oral quick-dissolving property of easily breaking down in the oral cavity and that do not cause problems during manufacture such as incomplete hardening of the shell or being crushed. The plasticizer may be glycerin.

DETAILED DESCRIPTION OF THE INVENTION

Figure 1:
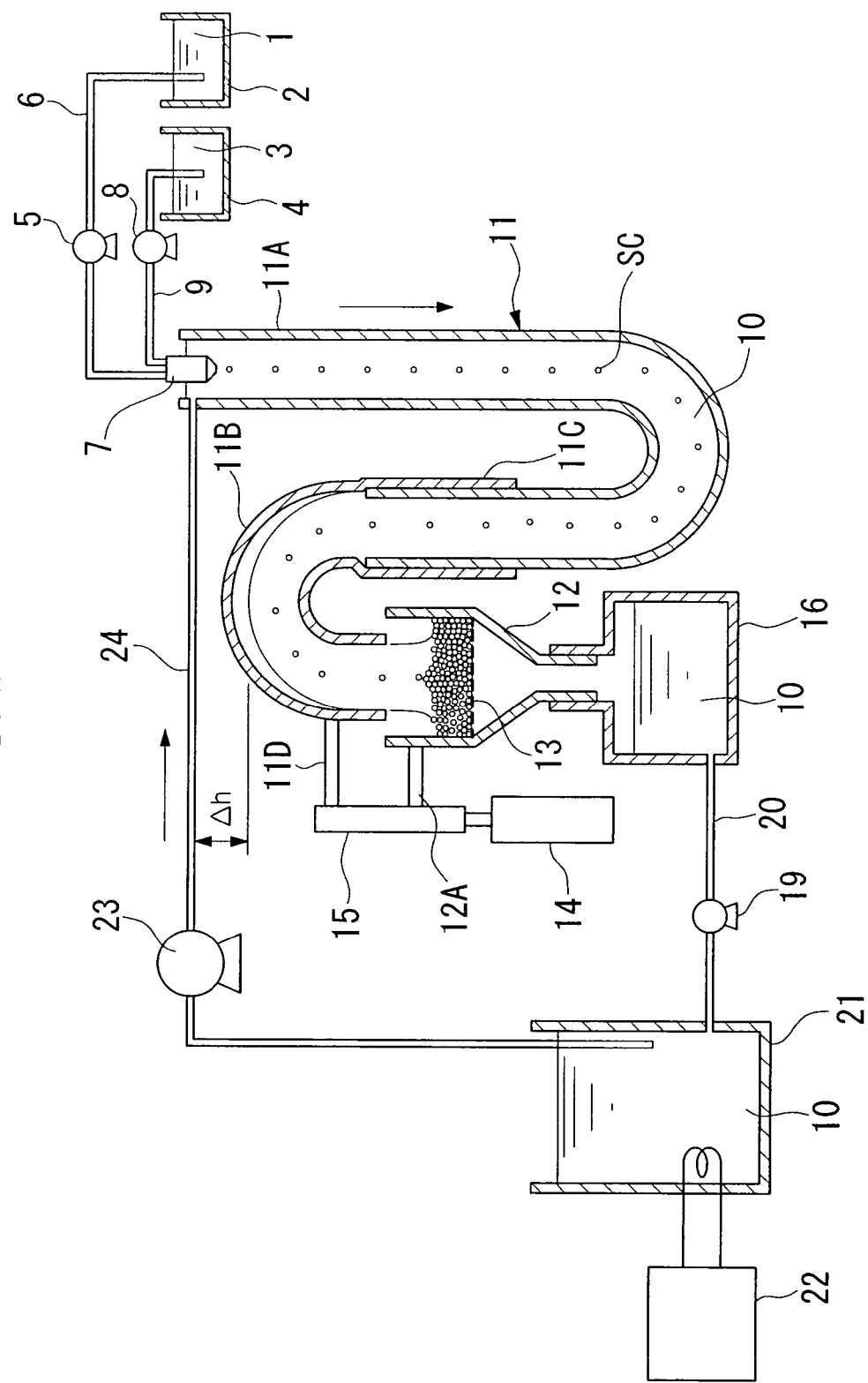
FIG. 1 is a schematic drawing of the in-liquid nozzle type seamless capsule manufacturing apparatus that can be used in the embodiments of the present invention.

Below, embodiments of the present invention will be explained in detail. However, the present invention is not limited by following embodiments, and various modifications within the scope of the claims are possible without departing from the spirit thereof.

In order to obtain the oral quick-dissolving property of easily breaking in the oral cavity, the inventors carried out several investigations of various types of capsules such as hard capsules, soft capsules, and seamless capsules. The oral quick-dissolving property could not be obtained from the hard capsule because they only swelled in the mouth without breaking. Due to manufacturing considerations, the shell material of soft capsules must comprise 30% by mass of the total mass. Furthermore, in a seamless capsule, the dissolving properties deteriorate using gelatin alone. However, the ratio of shell material to mass of the capsule was lowest for seamless capsules, and thus seamless capsules were found to be most suitable as oral quick-dissolving capsules. Generally, a plasticizer is added to the gelatin of the shell material, and a water-soluble plasticizer is suitable as a plasticizer for use in oral quick-dissolving capsules.

As a result of these investigations, the inventors discovered that seamless capsules are especially superior as oral quick-dissolving capsules when formed within the following ranges: capsule diameter, 1 to 10 mm; a mass ratio of shell material to filler material, 5:95 to 70:30; and using one or more plasticizer selected from a group consisting of glycerin, propylene glycol, or polyethylene glycol added at 20 to 70% by mass with respect to the shell material as a whole (excluding water).

Furthermore, the inventors established a manufacturing method for oral quick-dissolving seamless capsules that allows the manufacture of the product in which problems of such as incomplete hardening of the shell or being crushed during manufacture occur with difficulty.

The manufacturing method for the seamless capsules of this embodiment comprises the following steps:

Step A: preparing the core liquid that includes the filler material and the shell liquid in which a shell material is dissolved.

Step B: using a coaxial multiple nozzle having the inner nozzle and the outer nozzle that surrounds the inner nozzle, supplying the core liquid to the inner nozzle and the shell liquid to the outer nozzle so as to extrude them, and forming multilayer liquid drops by extruding a multilayer jet from the coaxial multiple nozzle.

Step C: hardening the shell liquid while the multilayer liquid drops flow in a hardening liquid that flows through a pass, and forming seamless capsules in which the core liquid is surrounded by the shell material.

Step D: separating the seamless capsules from the hardening liquid that surrounds them.

Step E: eliminating the hardening liquid adhering to the surface of the seamless capsules that have been separated from the hardening liquid, and at the same time forming seamless capsules that do not substantially stick to each other by drying their surfaces.

By carrying out steps A through E in sequence, the filler material is covered by a shell material that includes the shell forming agent such as gelatin and the plasticizer such as glycerin, and seamless capsules are manufactured having a particle diameter of 1 to 10 mm and a mass ratio of shell material to filler material in the range of 5:95 to 70:30. Below, examples of each of the steps will be explained in detail.

[Step A]

In the present invention, the filler material can be in a liquid state when extruded from the multiple nozzle in step B as the core liquid, and the core liquid can remain a liquid after the formation of the multilayer liquid drops, or alternatively can be a gel or solid after formation of the seamless capsule. In addition to the main component (the effective ingredient in the case of a pharmaceutical) such as a foodstuff, health food, flavoring, condiments, pharmaceutical, aromatic agent, or the like, it is possible to include various additives such as solvents (for example, edible oils), sweeteners, souring agents, flavorings, colorings, thickeners (gelatinizing agents), stabilizers, and emulsifiers, or the like that are permitted in terms of food production or pharmacology. When the filler material is prepared in a liquid state, it can take the form of a transparent solution, suspension, or a latex (cream) where the main component is dissolved in a solvent. The method in which a liquid filler material, that is, a core liquid, is prepared can be any well-known method in the fields of food production or pharmaceutical manufacturing. For example, to prepare a transparent core liquid, the main component and additives are measured and mixed with a solvent such as a edible oil, and as needed heated and agitated to produce a uniform solution.

To prepare an emulsified core liquid, well-known conventional methods can be used in which the main component, including an emulsifying agent, and an oil component are emulsified using a homogenizer to obtain an oil-in-water emulsion. Materials such as super-sweet sweeteners, for example, aspartame or sucralose, that can be dispersed and dissolved in ethanol have large particle diameters when dispersed directly in oil, which causes the capsule formation properties to become unstable. Thus, a method can be used wherein first these are dispersed and dissolved in ethanol using a homogenizer, and then dissolved in oil.

In the present invention, the shell material includes one or a plurality of shell forming agents such as gelatin or agar that are permitted in terms of food production or pharmacology and a plasticizer for softening the film after hardening and for lowering the shell strength in the oral cavity so that the shell layer will break easily therein. One or more plasticizer selected from a group consisting of glycerin, propylene glycol, polyethylene glycol can be used as the plasticizer, and among these glycerin is suitable as a plasticizer. The added amount of this plasticizer is 20 to 70% by mass with respect to the total amount of the shell material (the total amount of the components of the shell liquid excluding water), preferably 30 to 65% by mass, and more preferably 40 to 60% by mass. By mixing glycerin in the shell material within these ranges, the shell becomes pliable after hardening, and dissolves easily in the oral cavity.

To adjust the hardness of the shell, a material that increases the hardness of the shell material after hardening, such as sorbitol, can be added to the shell material along with the plasticizer. Furthermore, by adding a thickening polysaccharide, a gelling agent, a proteolytic agent or the like, it is possible to improve the long-term stability of the shell. The shell material can be colored to any arbitrary color tone by a pigment, and flavorings, sweeteners, souring agents or the like can be added. Sorbitol, thickening polysaccharides, gelling agents, proteolytic agents and the like are added at 10% by mass or less with respect to the total amount of the shell material, and preferably at 5% by mass or less.

The shell liquid is prepared by adding an appropriate amount of water to the shell material that includes at least the shell forming agent and the plasticizer, and being dissolved into the water by heating. The amount of the shell material (that is, the total amount of components excluding water) mixed into the shell liquid is 10 to 50% by mass with respect to the total amount of the shell liquid, and preferably 20 to 40% by mass. In the case of gelatin, the amount of shell forming material is 15 to 35% by mass with respect to the total amount of the shell liquid, and preferably 20 to 30% by mass.

The method of adding water to the shell forming agent and dissolving it by heat is not limited. For example, a method in which water is added to the film forming agent and it is dissolved by heating after swelling, or a method in which the shell forming agent is injected into heated water and dissolved by agitation can be used. In this heated water-agitation dissolving method, the adjustment of the liquid can be done in a short time. The heating temperature is set according to the type of shell forming agent used, and for example, in the case of gelatin, is 45 to 90° C., and preferably, 45 to 55° C. In order to prepare the shell liquid so as not to incorporate bubbles, preferably the shell liquid is prepared while the shell material and water are injected into a heated reduced-pressure tank, and heated and agitated under a reduced atmosphere.

The core liquid and the shell liquid prepared as described above are stored in a suitable vessel such as separate storage tanks. The shell liquid must be cooled and maintained at a temperature that does not cause gelling. The storage temperature of the shell liquid is set depending on the type of shell forming agent that is used, and for example, in the case of gelatin, is 45 to 90° C., and preferably 45 to 55° C. With regards to the prepared amounts of the core liquid and the shell liquid, in the completed seamless capsules, preferably the mass ratios of the shell material and the filler material are prepared at a mass ratio set between 5:95 to 70:30.

[Step B to step D]

Steps B to D can be carried out continuously by using a conventionally well-known seamless capsule manufacturing apparatus. FIG. 1 is a schematic drawing showing an example of a suitable manufacturing apparatus for continuously carrying out steps B to D of the manufacturing method for seamless capsules of the present invention.

In the in-liquid nozzle type seamless capsule manufacturing apparatus in FIG. 1, the core liquid (the inner layer liquid) 1 for forming the seamless capsules is stored in the core liquid tank 2, and the shell liquid (the outer layer liquid) 3 for covering the core liquid 1 is stored in the shell liquid tank 4.

The core liquid 1 is delivered under pressure to the multiple nozzle 7 via the duct 6 from the core liquid tank 2 by the pump 5, and the shell liquid 3 is delivered under pressure to the multiple nozzle 7 via the duct 9 from the shell liquid tank 4 by the pump 8.

The multiple nozzle 7 is formed so as to be inserted into the opening of the flow duct 11, that is, the inflow portion 11A of the hardening liquid 10, and generate multilayer liquid drops by extruding the core liquid 1 and the shell liquid 3 into the hardening liquid 10 in the flow duct 11.

The hardening liquid 10 cools and hardens the generated multilayer liquid drops to form the seamless capsules SC. When the shell liquid is hardened by cooling, edible oils such as medium chain triglycerides (MCT) can be used as a hardening liquid, or a hardening liquid can be used whose property of preventing sticking between multilayer liquid drops is improved by adding a surfactant such as lecithin to this MCT. The temperature of the hardening liquid is set at 0° C. to room temperature.

In the present apparatus, the flow duct 11 is formed as a curved cylinder consisting of a substantially J-shaped inflow part 11A and an inverted J-shaped outflow part 11B that engages the inflow part 11A by being inserted therein so as to be able to slide while forming an air-tight seal by the engagement part 11C. Therefore, as will be described below, the flow duct 11 is formed so that the inflow part 11A and the outflow part 11B can move relatively to each other at the engagement part 11C. In particular, the present apparatus is structured so that the outflow part 11B moves vertically.

A substantially funnel-shaped separator 12 is disposed below the outlet end of the outflow part 11B of the flow duct 11. This separator 12 separates the seamless capsules SC and the hardening liquid 10 that flow out together from the flow duct 11. Inside the separator 12, a mesh 13 is stretched out through which only the hardening liquid 10 passes, not the seamless capsules SC.

The separator 12 moves vertically with the outflow part 11B of the flow duct 11 by, for example, a pressure flow cylinder such as an air cylinder or hydraulic cylinder, or a motor. Specifically, a part of the outflow part 11B of the flow duct 11 is joined to a connecting rod 11D while the separator 12 is joined to the connecting rod 12A. Furthermore, the connecting rods 11D and 12A are joined to a connecting member 15, and this connecting member 15 is joined to a part of the drive source 14, such as the piston rod of an air cylinder.

Therefore, when the drive source 14 is activated, and, for example, the piston rod of an air cylinder moves reciprocally in the vertical direction, the outflow part 11B of the flow duct 11 and the separator 12 move vertically together equal distances due to the connecting member 15 and each of the connecting rods 11D and 12A.

Thereby, the difference $\Delta h$ between the heights of the liquid surface of the inflow part 11A and the liquid surface of the outflow part 11B of the flow duct 11 can be adjusted, and thereby the flow rate of the hardening liquid 10 in the flow duct 11 can be adjusted.

Further, because the outflow part 11B of the flow duct 11 and the separator 12 move vertically together, a constant difference is maintained between the height of the liquid surface of the hardening liquid 10 in the outflow part 11B and the separator 12 (in particular, the mesh 13 thereof).

In the separator 12, the hardening liquid 10 separated from the seamless capsules SC is recovered in the separation tank 16 therebelow.

The small diameter part at the bottom end of the separator 12 engages with the cylinder part of the upper end of the separation tank 16, and the separator 12 is structured so that even if it moves vertically, it does not separate from the separation tank 16.

The hardening liquid 10 inside the separation tank 16 is delivered under pressure to the cooling tank 21 via the duct 20 by the pump 19. The hardening liquid 10 inside the cooling tank 21 is cooled to a predetermined temperature, and then is returned into the flow duct 11 via the duct 24.

This seamless capsule manufacturing apparatus has an in-liquid nozzle structure, and thus the multiple nozzle 7 is structured such that it is inserted into the entrance part of the flow duct 11 that forms the flow path for supplying the hardening liquid 10, the core liquid 1 and the shell liquid 3 are extruded into the liquid, and the latter encapsulates the former completely.

Therefore, in the present embodiment, the core liquid 1 and the shell liquid 3 that are extruded from the multiple nozzle 7 are formed into multilayer liquid drops in the hardening liquid 10 in the flow duct 11 (step B), and they are cooled and hardened by the action of the hardening liquid 10 as they flow through the flow duct 11 (step C). Next, the seamless capsules SC formed in this manner flow down along with the hardening liquid 10 onto the mesh 13 of the separator 12 from the exit end of the outflow part 11B of the flow duct 11, and are separated from the hardening liquid 10 by the mesh 13 (step D). The hardening liquid 10 passes through the mesh 13 to be recovered in the separation tank 16. The seamless capsules SC that have accumulated on the mesh 13 are later recovered in a product recovery vessel (not illustrated) in batch when an appropriate amount has been accumulated.

In the present apparatus, when the difference Δh between the heights of the liquid surfaces in the inflow part 11A and the outflow part 11B of the flow duct 11 are adjusted, the outflow part 11B of the flow duct 11 can move vertically with respect to the outflow part 11A due to the drive source 14, and thus by arbitrarily changing the difference Δh between the heights of the liquid surfaces at the lower position and the upper position, the flow rate of the hardening liquid 10 in the flow duct 11 can be adjusted to an arbitrary optimal position.

In the present apparatus, because the outflow part 11B of the flow duct 11 and the separator 12 are vertically moved together equal distances, a constant difference is maintained between the liquid surface of the hardening liquid 10 in the outflow part 11B and the separator 12. Therefore, the seamless capsules SC in the present embodiment always have the desired spherical shape, and furthermore, breakage and leaking of the seamless capsules SC can be prevented. In the present invention, the particle diameter of the seamless capsules SC is 1 to 10 mm. Seamless capsules SC having a particle diameter in this range are easily manufactured, they are easily handled by the user, and they are an appropriate size for oral use.

In particular, in the present apparatus, the outflow part 11B of the flow duct 11 and the separator 12 have an integral structure in which the connecting rods 11D and 12A are structurally bound together to the connecting member 15, and this integral structure is moved as a whole vertically by a drive source such as a pressure flow cylinder. Thereby, the outflow part 11B and the separator 12 are always reliably moved vertically by an equal distance. This structure is simple and inexpensive.

In step B, in addition to the coaxial double nozzle, a coaxial triple nozzle can also be used, and in addition to the nozzle oscillating method, the oscillating method necessary for generating the multilayer liquid drops includes various methods such as ring oscillation methods and tube oscillation methods as well. Of course, instead of a multiple nozzle, a single nozzle that extrudes a liquid drop having only a single layer can be used.

In step B, preferably a multiple nozzle 7 is used whose distal angle (the angle of the conical part) is equal to or less than 90°. By using a multiple nozzle 7 whose distal angle is equal to or less than 90°, no turbulence occurs in the flow of the hardening liquid that flows in contact with the distal end of the multiple nozzle 7, and seamless capsules SC having uniform particle diameters can be formed.

In step B, the respective distal ends of the outer nozzle and the inner nozzle of the multiple nozzle 7 can be disposed on the same plane, or a structure can be used wherein the distal end of the inner nozzle protrudes out 1 to 5 mm from the distal end of the outer nozzle.

In step B, the position of the distal end of the multiple nozzle 7 can be aligned with the central axis of the flow duct 11, or can be disposed eccentric to the central axis. In the case that the position of the distal end of the multiple nozzle 7 is aligned with the central axis of the flow duct 11, the multilayer liquid drops extruded from the multiple nozzle 7 drop straight down along the central axis of the multiple nozzle 7. In contrast, in the case that the position of the distal end of the multiple nozzle 7 is disposed eccentric to the central axis, the multilayer liquid drops fall along a spiral shaped path in proximity to the inner wall of the flow duct 11, and thereby it is possible to lengthen the amount of time of the downward flow of the multilayer liquid drops. By making the position of the multiple nozzle 7 variable with respect to the central axis of the flow duct 11, it is possible to adjust the finished state of the seamless capsules, and it is possible to obtain a high quality product by preventing the occurrence of irregularities in thickness and eyes. "Eyes" are small liquid cells formed in a shell layer. If the size of eyes are large, the risk will arise that a hole is generated in the shell layer after drying the shell layer, and core liquid flows out of microcapsule.

In steps B and C, a structure is preferable wherein a stroboscope is disposed at a position along the flow duct 11, and thereby the particle diameter and shape of the multilayer liquid drops flowing down through the flow duct 11 can be monitored. By monitoring the multilayer liquid drops using a stroboscope in this manner, it is possible to rapidly adjust the extrusion conditions of each liquid from the multiple nozzle 7, the oscillation conditions, the flow rate of the hardening liquid, and the like so as to make the particle diameter of the seamless capsules to be manufactured, and it is possible to manufacture without waste seamless capsules having the object particle diameter without irregularities in thickness or eyes.

In step C, preferably a structure is used in which the hardening liquid 10 flows in the flow duct 11 through the entire circumference of the upper end of the flow duct 11, and thereby the hardening liquid 10 uniformly flows into the end of the flow duct 11 from all directions. Due to the hardening liquid 10 flowing in through the entire circumference of the end surface of the flow duct 11, it is possible to prevent the occurrence of local turbulence in the hardening liquid flow inside the flow duct 11.

In step C, preferably a dehydration device that eliminates water from the circulating hardening liquid 10 is provided at a location in contact with the hardening liquid 10. There is the possibility that atmospheric water or water from the multilayer liquid drops will become mixed with the hardening liquid 10. When the amount of water in the hardening liquid increases, there is the concern that problems such as the deformation of the shell, the capsules sticking together easily, and variations in the state of hardness of the shell liquid will occur. By providing a dehydration device that decreases as much as possible the amount of water in the hardening liquid 10, it becomes possible to manufacture high quality seamless capsules stably. The dehydration device can be a water absorption type, a cooling trap type, a microwave heating type or the like, and normally a simple device in which the hardening liquid 10 is brought into contact with an absorbent material such as silica gel is used.

In step D, instead the seamless capsules SC flowing down with the hardening liquid 10 onto the mesh 13 of the separator 12 and the seamless capsules SC being separated from the hardening liquid 10 using a mesh 13, a structure can be used wherein a separating and conveying apparatus provided with a conveyor belt made of mesh or a cloth filter is used, the efflux from the flow duct 11 is received by the conveyor belt, the hardening liquid falls through and is recovered, and only the seamless capsules SC are conveyed on the conveyor belt. By using such a separating and conveying apparatus, it is possible to prevent the problem of the separated seamless capsules SC piling up and deforming or crushing the capsules beneath them.

[Step E]

Seamless capsules manufactured by steps B through D described above and separated from the hardening liquid have the hardening liquid adhering to the surface thereof removed in step E, and by drying their surface, seamless capsules are formed without substantially sticking to each other. In the preferred embodiments of the present invention, the step E provides the following sub-steps e1 to e7.

Step e1: seamless capsules separated from the hardening liquid in step D are cooled either as they are or by being immersed in a coolant liquid consisting of a fluid that does not dissolve the shell, and specifically maintained between 0° C. and 20° C., and preferably between about 1° C. and 10° C., and thereby the hardening of the shell is promoted.

Step e2: the cooled seamless capsules are centrifuged, thereby eliminating the liquid adhering to the surface of the capsules;

Step e3: the centrifuged capsules are dried;

Step e4: the dried seamless capsules are cleaned with an organic solvent;

Step e5: the seamless capsules that have been cleaned in an organic solvent are dried;

Step e6: seamless capsules that have completed step e5 are sieved and graded;

Step e7: after drying, sieving, and grading, the seamless capsules are packaged.

In step e1, the cooling method is not particularly limited. It is possible to use, for example, a method in which the seamless capsules that have been separated from the hardening liquid are placed in a tray, a cooling liquid is put therein, each tray is placed in a refrigerator, and they are cooled for a certain period of time; a method in which the seamless capsules are conveyed on a conveyor to be cooled by passing through a tunnel shaped cooler; or a method in which the seamless capsules are brought into contact with a cooling plate. Preferably, a material that does not soften, dissolve, or destroy the shell is used as the cooling liquid. Examples are edible oils such as medium chain triglycerides, or an edible oil that includes a surfactant such as lecithin.

In step e1, by using a cooling temperature of about 2° C., freezing of the water in the capsule shell can be prevented, and at the same time, hardening of the capsule shell can be promoted.

In step e2, the centrifuging conditions are that a liquid such as oil that adheres to the shell of the seamless capsules is removed in a manner that does not effect the external appearance, and that the revolution speed and time do not deform or break the shell. The oil on the surface of the seamless capsules is removed as much as possible by this centrifuging, and thereby the drying efficiency in the next drying step e3 is improved, and the time required for drying can be shortened.

In step e2, instead of a process in which oil is removed from the surface of the seamless capsules by centrifuging, the oil on the shell surface can be removed by a process in which the capsules are wiped by a cloth, paper treated so as to become lipophilic, a non-fiber cloth, or the like.

In step e3, the drying method is not particularly limited. Drying can be implemented using methods and apparatuses conventionally used to dry particulate matter. For example, the forced-air drying method (including the fluidized bed drying method), the drum drying method, a reduced pressure drying method, and the like can be used. In the case of the forced-air drying method and the drum drying method, the seamless capsules are brought into contact with an air current equal to or less than the temperature at which the shell softens, preferably 0 to 40° C., and more preferably 10 to 30° C.

In step e3, in the case of using a drum drying method, preferably a baffle is provided that prevents slipping of the seamless capsules inside the drum. When the seamless capsules slip inside the drum, there is the concern that the drying state becomes irregular and thus that seamless capsules that are not completely dried will be produced.

In step e3, in the case of using a continuous-current drying method and the drum drying method, the temperature of the introduced air can be the same from the beginning to the end of the drying (for example, air at room temperature), or the temperature can be varied during the drying. For example, drying can be carried out using an initial cold air equal to or less than 25° C. at the start of the drying and then supplying air equal to or greater than 25° C. after the passage of a predetermined amount of time. Preferably, the introduced air has a low humidity, and thus as necessary air can be supplied that has been dried by passing through a water absorbing layer such as a silica gel.

In step e3, in the case of using the forced-air or a drum drying method, an aeration plate that carries the seamless capsules and the openings in the drum are preferably selected depending on the particle diameter of the seamless capsules.

In step e4, the organic medium used in order to clean the seamless capsules can dissolve the oils (hardening liquid, cooling liquid) that adhere to the seamless capsules. Any organic solvent that does not soften, dissolve, or destroy the shell can be used, and preferably carbohydrates such as ethyl alcohol, ethyl acetate, acetone, hexane, or mixtures thereof are used.

In step e4, the method of cleaning the seamless capsules using the organic solvent is not particularly limited. A method such as immersing the seamless capsules into the organic solvent and lifting them out, a method in which drops or a mist of the organic solvent is dispensed onto the seamless capsules, or the like can be used. The temperature of the organic solvent is about 0 to 40° C., and preferably room temperature. The number of cleanings and the cleaning time are not particularly limited. Cleaning can be carried out one time or repeated a plurality of times. During this cleaning operation, the cleaning efficiency can be improved by agitation or the application of ultrasound to a degree that does not damage the shell of the seamless capsules. The organic solvent is recovered and purified after the cleaning, and reused.

The drying in step e5 (second drying) is carried out mainly to remove the organic solvent from the seamless capsules after cleaning by the organic solvent. This cleaning method is not particularly limited, and can be implemented by using methods and apparatuses conventionally employed to dry particulate matter. For example, the forced-air method (including the fluidized bed drying method), the drum drying method, reduced pressure drying method, centrifuge drying method and the like can be used. The temperature, humidity, and devices are preferably substantially identical to those of the dying step in step e3. The exhaust gas that includes the organic solvent from the drying apparatus undergoes a solvent removal process by being brought into contact with a cooling trap or an appropriate solvent absorbent.

In step e6, the method of sieving and grading the seamless capsules after completion of the second drying step (step e5) can be carried out using methods employed in the product inspection of particulate matter, in particular for encapsulated pharmaceuticals for soft capsules. Inspection categories for the seamless capsules may include the size of the particle diameter, and the presence or absence of abnormally shaped product, broken shell, cloudiness and contaminants, and products with bad external appearance irregularities in thickness, eyes or the like, and fused capsules. With regards to the filler material, various necessary analytic tests in terms of pharmaceutical production and food hygiene are carried out for leaking of the seamless capsules.

In step e7, after completion of the drying and before packaging the seamless capsules after sieving and grading, suitable amounts of a starch such as lactose, mannitol, powdered oblate, corn starch or the like can be sprinkled on the surface of the capsules to prevent sticking, and blocking prevention of the capsules can be implemented Moreover, the embodiments described above are simply to illustrate examples of the present invention, and the present invention can be modified in various ways without departing from the scope thereof.

EXAMPLES

Below, the effect of the present invention will be clarified by examples. However, the present invention is not limited by the examples described below.

Medium chain triglycerides were used as a fill liquid (core liquid) and shell liquids was used having a mixture of 30% by mass of the shell material consisting of each of the compounds listed in Table 1 and 70% by mass of water. Using the seamless capsule manufacturing apparatus "Spherex" (a registered trademark of Freund Inc.), multi-layer liquid drops were dropped at a speed of 4 to 20 per second from the multiple nozzle thereof into a hardening liquid consisting of a cooled medium chain triglyceride to manufacture seamless capsules having each of the compositions of Nos. 1 to 6 shown in Table 1.

For each of the manufactured capsules Nos. 1 to 6, disintegration tests were carried out according to the disintegration test of Japanese pharmacopoeia.

TABLE 1

Disintegration property of capsule with respect to water at 37° C.

| | No. | | | | | |
|---|---|---|---|---|---|---|
| | 1 | 2 | 3 | 4 | 5 | 6 |
| Capsule Diameter (mm) | 5 | 5 | 5 | 5 | 5 | 5 |
| Gelatin (% by mass) | 6 | 8 | 12 | 16 | 18 | 27 |
| Glycerin (% by mass) | 4 | 2 | 8 | 4 | 2 | 3 |
| Shell (% by mass) | 10 | 10 | 20 | 20 | 20 | 30 |
| Fill Liquid | Medium Chain Triglycerides | Medium Chain Triglycerides | Medium Chain Triglycerides | Medium Chain Triglycerides | Medium Chain Triglycerides | Medium Chain Triglycerides |
| Fill Liquid (% by mass) | 90 | 90 | 80 | 80 | 80 | 70 |
| Disintegration Time (Seconds) (*1) | 7 | 10 | 10 | 60 | 120 | 300 |
| Comments | Dissolved Quickly | Dissolved Quickly | Dissolved Quickly | Took Time To Dissolve Compared To No. 3 | Took Time To Dissolve Compared To No. 4 | Took Much Time To Dissolve |
| Disintegration Properties | Good | Good | Good | Difficult | Bad | Bad |

(*1) Time to disintegration of the capsule (n = 6)

From the results of Table 1, the seamless capsules Nos. 1 to 3 according to the present invention are superior in terms of disintegration properties, and appropriate for use as oral quick-dissolving capsules.

In comparison to seamless capsule No. 3, seamless capsule No. 4 requires time before breaking down.

Seamless capsules No. 5 and 6 require even more time before breaking down, and are not suitable as oral quick-dissolving capsules.

What is claimed is:

1. A manufacturing method for oral quick-dissolving seamless capsules, comprising the steps of:
   preparing a core liquid containing a filler material;
   preparing a shell liquid containing a shell material that includes one or more plasticizers selected from the group consisting of glycerin, propylene glycol, and polyethylene glycol, and a shell forming agent;
   supplying to a multiple nozzle, which has an inner nozzle and an outer nozzle that surrounds the inner nozzle, the core liquid so as to be extruded from the inner nozzle, and the shell liquid so as to be extruded from the outer nozzle, in order to form multilayer liquid drops by extruding a multilayer jet from the multiple nozzle;
   forming seamless capsules by hardening the shell liquid of the multilayer liquid drops by reacting the shell liquid with a hardening liquid flowing through a passage, and coating the core liquid with the shell material;
   separating the seamless capsules from the hardening liquid; and
   removing the hardening liquid adhering to surfaces of the seamless capsules separated from the hardening liquid and drying the surfaces to form seamless capsules that do not substantially adhere to each other;
   wherein the seamless capsules are manufactured to have a particle diameter of 1 to 8 mm, a mass ratio of the shell material to the filler material of 5:95 to 20:80, and an amount of added plasticizer is 40 to 70% by mass with respect to the total amount of the shell material, excluding water.

2. A seamless capsule manufacturing method according to claim 1, wherein the amount of the plasticizer is 40 to 65% by mass with respect to the total amount of the shell material, excluding water.

3. A seamless capsule manufacturing method according to claim 1, wherein the amount of the plasticizer is 40 to 60% by mass with respect to the total amount of the shell material, excluding water.

4. A seamless capsule manufacturing method according to claim 1, wherein the shell material includes sorbitol in an amount of no more than 10% by mass.

5. A seamless capsule manufacturing method according to claim 1, wherein the shell material includes at least one of a polysaccharide, a gelling agent, and a proteolytic agent, in an amount of no more than 10% by mass.

6. A seamless capsule manufacturing method according to claim 1, wherein the hardening liquid includes an edible oil.

7. A seamless capsule manufacturing method according to claim 1, wherein the seamless capsules are manufactured to have a particle diameter of 1 to 7 mm.

8. A seamless capsule manufacturing method according to claim 1, wherein the mass ratio of the shall material to the filler material is 5:95 to 15:85.

* * * * *